United States Patent
Amemiya et al.

(10) Patent No.: US 9,410,984 B2
(45) Date of Patent: Aug. 9, 2016

(54) SURFACE FORCE MEASURING METHOD AND SURFACE FORCE MEASURING APPARATUS

(71) Applicant: ELIONIX INC., Tokyo (JP)

(72) Inventors: Hironao Amemiya, Tokyo (JP); Hayato Kobayashi, Tokyo (JP); Takahisa Kato, Tokyo (JP)

(73) Assignee: ELIONIX INC., Tokyo (JP)

( * ) Notice: Subject to any disclaimer, the term of this patent is extended or adjusted under 35 U.S.C. 154(b) by 0 days.

(21) Appl. No.: 14/762,261

(22) PCT Filed: Jan. 16, 2014

(86) PCT No.: PCT/JP2014/050666
§ 371 (c)(1),
(2) Date: Jul. 21, 2015

(87) PCT Pub. No.: WO2014/115634
PCT Pub. Date: Jul. 31, 2014

(65) Prior Publication Data
US 2015/0362525 A1    Dec. 17, 2015

(30) Foreign Application Priority Data
Jan. 28, 2013 (JP) .................................. 2013-012876

(51) Int. Cl.
*G01Q 60/24* (2010.01)
*G01Q 10/06* (2010.01)
(Continued)

(52) U.S. Cl.
CPC ............... *G01Q 60/38* (2013.01); *G01Q 10/00* (2013.01); *G01Q 20/04* (2013.01); *G01N 2203/0286* (2013.01)

(58) Field of Classification Search
CPC ..... B82Y 32/00; G01Q 10/065; G01Q 20/00; G01Q 60/38; G01Q 60/34; G01Q 60/28; G01Q 60/363; Y10S 977/732; Y10S 977/86; Y10S 977/865; Y10S 977/875

USPC ........... 850/7, 5, 6, 33, 56, 10, 18, 37, 40, 57, 850/59, 9
See application file for complete search history.

(56) References Cited

U.S. PATENT DOCUMENTS 5,461,907 A * 10/1995 Tench ..................... B82Y 35/00
                                                      73/105
6,249,000 B1 * 6/2001 Muramatsu ............ B82Y 35/00
                                                      73/105
(Continued)

FOREIGN PATENT DOCUMENTS

| JP | 6-11435 | 1/1994 |
| JP | 9-72925 | 3/1997 |

(Continued)

OTHER PUBLICATIONS
International Search Report (ISR) issued Feb. 10, 2014 in International (PCT) Application No. PCT/JP2014/050666.

*Primary Examiner* — David A Vanore
(74) *Attorney, Agent, or Firm* — Wenderoth, Lind & Ponack, L.L.P.

(57) ABSTRACT

The present invention provides a method and an apparatus for measuring a force (which will be referred to as surface force) acting between two material surfaces. A surface force measuring method includes moving an object (1) toward a probe (4) until the probe (4) is adsorbed to the object (1), then applying a load from an electromagnetic-force generator (20) to a supporting member (6) in a direction as to separate the probe (4) from the object (1) while gradually increasing an electric current supplied to the electromagnetic-force generator (20), obtaining a value of the electric current supplied to the electromagnetic-force generator (20) when the probe (4) is separated from the object (1), and converting the value of the electric current into a surface force acting between the probe (4) and the object (1).

10 Claims, 5 Drawing Sheets

(51) Int. Cl.
  *G01Q 60/38* (2010.01)
  *G01Q 20/04* (2010.01)
  *G01Q 10/00* (2010.01)

(56) References Cited

U.S. PATENT DOCUMENTS

| | | | | |
|---|---|---|---|---|
| 6,297,502 B1* | 10/2001 | Jarvis | .................... | B82Y 35/00 73/105 |
| 8,434,160 B1* | 4/2013 | Adams | .................. | G01Q 70/08 250/234 |
| 8,650,660 B2* | 2/2014 | Shi | ....................... | G01Q 10/065 850/5 |
| 9,213,047 B2* | 12/2015 | Li | .......................... | G01Q 20/00 |
| 2002/0005481 A1* | 1/2002 | Williams | .............. | B82Y 35/00 250/306 |
| 2011/0055983 A1* | 3/2011 | Kawakatsu | ............ | B82Y 35/00 850/5 |
| 2013/0047302 A1* | 2/2013 | Noel | ...................... | B82Y 35/00 850/6 |
| 2013/0047303 A1* | 2/2013 | King | ...................... | B82Y 35/00 850/56 |
| 2013/0276174 A1* | 10/2013 | Li | .......................... | B82Y 35/00 850/6 |
| 2015/0362525 A1* | 12/2015 | Amemiya | .............. | G01Q 20/04 850/40 |

FOREIGN PATENT DOCUMENTS

| | | |
|---|---|---|
| JP | 2001-108603 | 4/2001 |
| JP | 2003-161684 | 11/2001 |
| JP | 2006-284598 | 10/2006 |
| JP | 2011-38851 | 2/2011 |

* cited by examiner

SURFACE FORCE MEASURING METHOD AND SURFACE FORCE MEASURING APPARATUS

TECHNICAL FIELD

The present invention relates to a method and an apparatus for measuring a force acting between two material surfaces (hereinafter this force will be referred to as surface force).

BACKGROUND ART

Generally, there have been known a force curve measuring technique that uses an atomic force microscope (AFM: Atomic Force Microscope) and a measuring technique using a surface-force measuring device (see, for example, a patent document 1). When a probe, which is attached to a tip end of a cantilever (or cantilever spring), approaches an object to be measured (or a specimen), the probe is attracted to the object by a surface force acting between the object and the probe, and the probe is then brought into contact with the object. When the probe is forced in a direction away from the object, the probe continues to stay in contact with the object due to the surface force until the probe is separated from the object at a certain position. The surface force is calculated by multiplying an amount of flexure of the cantilever (i.e., a displacement of the probe) by a spring constant of the cantilever.

When the surface force is measured using the cantilever, a measurable range for the surface force depends on the spring constant of the cantilever. If the spring constant is too small relative to the surface force to be measured, the cantilever is bent to a large extent. When the cantilever is bent, the probe is displaced in a circular path around a fulcrum at which the cantilever is fixed. Therefore, a direction in which the probe is displaced does not align with a direction in which the surface force acts. As a result, an error between a measured value and an actual surface force may arise due to the fact that the direction in which the probe is displaced does not align with the direction in which the surface force acts, and such an error cannot be ignored. On the other hand, if the spring constant is too large relative to the surface force to be measured, a measurement error of the displacement of the probe may arise because the amount of flexure of the cantilever is small.

For the above reasons, in order to accurately measure the surface force using a cantilever, it is necessary to choose a cantilever having a spring constant suitable for a measurement range for the surface force. However, it is time-consuming to replace a cantilever with another for every measurement condition. Such disadvantages have been neither recognized nor suggested as problems.

CITATION LIST

Patent Literature

Patent document 1: Japanese laid-open patent publication No. 2001-108603
Patent document 2: Japanese laid-open patent publication No. 2003-161684

SUMMARY OF INVENTION

Technical Problem

The present invention has been made in order to solve the above disadvantages. It is an object of the present invention to provide a surface force measuring method and a surface force measuring apparatus which are capable of accurately measuring a surface force in a wide range.

Solution to Problem

In order to achieve the above object, there is provided a surface force measuring method using an apparatus that includes a supporting member, a probe secured to the supporting member, a spring mechanism resiliently holding the supporting member and allowing the supporting member to move only linearly, and an electromagnetic-force generator configured to generate an electromagnetic force for applying a load to the supporting member, the surface force measuring method comprising: moving an object, to be measured, toward the probe until the probe is adsorbed to the object; then applying a load from the electromagnetic-force generator to the supporting member in a direction as to separate the probe from the object while gradually increasing an electric current supplied to the electromagnetic-force generator; obtaining a value of the electric current supplied to the electromagnetic-force generator when the probe is separated from the object; and converting the value of the electric current into a surface force acting between the probe and the object.

In a preferred aspect of the present invention, the surface force measuring method further comprises, after the probe is adsorbed to the object, moving the probe and the object until the probe is returned to its initial position with the object kept in contact with the probe, wherein after the probe is returned to its initial position, the electromagnetic-force generator applies the load to the supporting member in the direction as to separate the probe from the object while the electric current supplied to the electromagnetic-force generator is gradually increased.

In a preferred aspect of the present invention, the surface force measuring method further comprises creating a vacuum in a space in which the object, the probe, the supporting member, the spring mechanism, and the electromagnetic-force generator are disposed.

In a preferred aspect of the present invention, the surface force measuring method further comprises regulating temperatures of the object, the probe, the supporting member, the spring mechanism, and the electromagnetic-force generator.

In a preferred aspect of the present invention, the value of the electric current is converted into the surface force using a predetermined relational expression which represents a correlation between the value of the electric current and the surface force.

According to another aspect of the present invention, there is provided a surface force measuring apparatus comprising: a supporting member; a probe secured to the supporting member; a spring mechanism resiliently holding the supporting member and allowing the supporting member to move only linearly; an electromagnetic-force generator configured to generate an electromagnetic force for applying a load to the supporting member; a displacement measuring device configured to measure a displacement of the probe; a first positioning mechanism configured to perform positioning of an object to be measured; a second positioning mechanism configured to perform positioning of the object more precisely than the first positioning mechanism; and an operation controller configured to control operations of the electromagnetic-force generator, the first positioning mechanism, and the second positioning mechanism, wherein the operation controller is configured to cause the second positioning mechanism to move the object toward the probe until the probe is adsorbed to the object, then cause the electromagnetic-force generator to apply a load to the supporting member in a direction as to separate the probe from the object while gradually increasing an electric current supplied to the electromagnetic-force generator, obtain a value of the electric current supplied to the electromagnetic-force generator when the probe is separated from the object, and convert the value of the electric current into a surface force acting between the probe and the object.

In a preferred aspect of the present invention, the operation controller is configured to cause the second positioning mechanism to move the probe and the object, after the probe is adsorbed to the object, until the probe is returned to its initial position with the object kept in contact with the probe.

In a preferred aspect of the present invention, the surface force measuring apparatus further comprises a vacuum chamber in which the object, the probe, the supporting member, the spring mechanism, the electromagnetic-force generator, the displacement measuring device, the first positioning mechanism, and the second positioning mechanism are disposed.

In a preferred aspect of the present invention, the surface force measuring apparatus further comprises a temperature regulator configured to regulate temperatures of the object, the probe, the supporting member, the spring mechanism, the electromagnetic-force generator, the displacement measuring device, the first positioning mechanism, and the second positioning mechanism.

In a preferred aspect of the present invention, the operation controller stores a predetermined relational expression which represents a correlation between the value of the electric current and the surface force, and is configured to convert the value of the electric current into the surface force using the predetermined relational expression.

Advantageous Effects of Invention

According to the present invention, the surface force is determined based on the electric current value at a moment the probe is separated from the object. No spring constant is required for calculating the surface force, and the surface force can be measured independently of any spring constant. Therefore, it is possible to measure surface forces in a wide range. In addition, since the spring mechanism allows the supporting member to move only linearly, the direction in which the probe is displaced is aligned with the direction in which the surface force acts. Therefore, the surface force can accurately be measured.

DESCRIPTION OF EMBODIMENT

Embodiment of the present invention will be described below with reference to the drawings.

Figure 1:
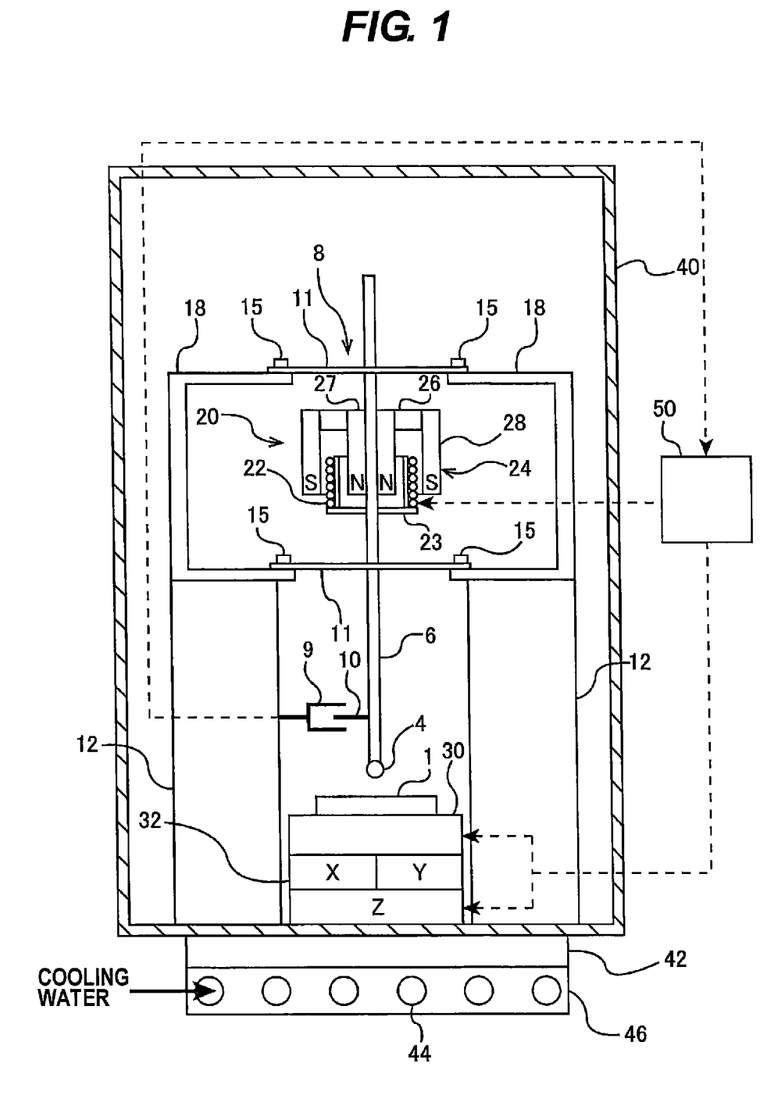
FIG. 1 is a schematic view showing an overall structure of a surface force measuring apparatus according to an embodiment of the present invention.

FIG. 1 is a schematic view showing an overall structure of a surface force measuring apparatus according to an embodiment of the present invention. As shown in FIG. 1, the surface force measuring apparatus includes a probe 4, a supporting rod (supporting member) 6 that supports the probe 4, a spring mechanism 8 that resiliently holds the supporting rod 6, an electromagnetic-force generator 20 configured to generate an electromagnetic force for applying a vertical load to the supporting rod 6, and a displacement measuring device 9 configured to measure a displacement of the probe 4. The supporting rod 6 extends in a vertical direction, and the probe 4 is secured to a distal end (or a lower end) of the supporting rod 6.

The spring mechanism 8 is supported by two support pedestals 12, 12. The displacement measuring device 9 is fixed to one of the two support pedestals 12, 12. A measurement target 10 is fixed to the supporting rod 6 so that the measurement target 10 is movable in vertical directions together with the supporting rod 6 and the probe 4. The displacement measuring device 9 measures a vertical displacement of the probe 4 from a vertical displacement of the measurement target 10. A non-contact type displacement sensor may preferably be used as the displacement measuring device 9.

Figure 2:
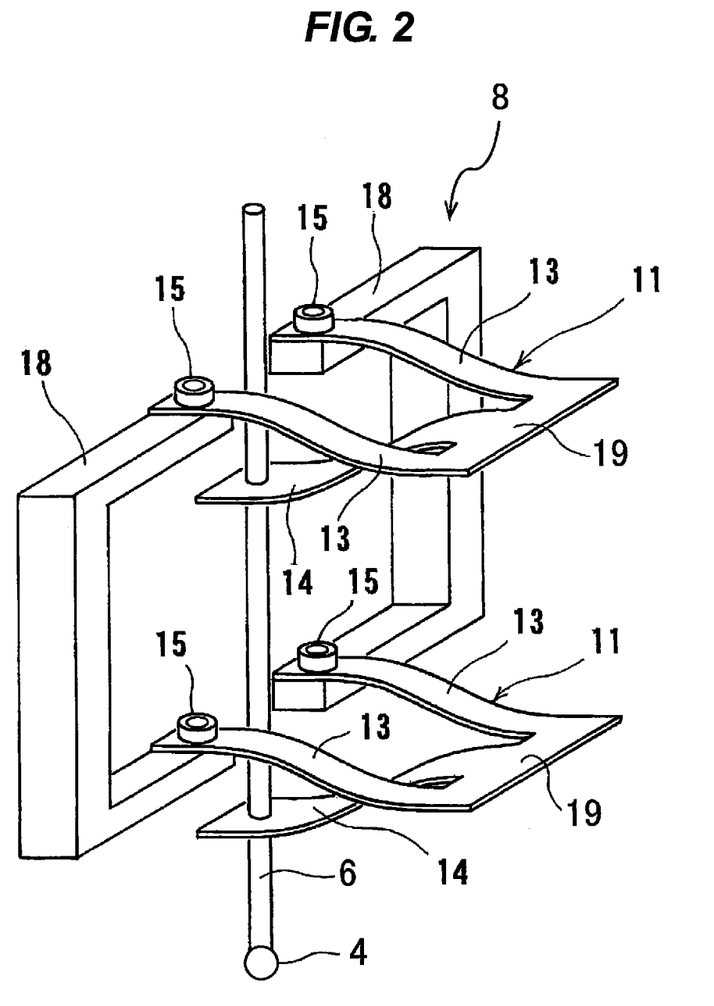
FIG. 2 is a perspective view showing details of a spring mechanism.

FIG. 2 is a perspective view showing details of the spring mechanism 8. As shown in FIG. 2, the spring mechanism 8 includes E-shaped leaf springs 11, 11, bolts 15, and fixed frames 18, 18. The supporting rod 6 is resiliently held by the E-shaped leaf springs 11, 11. The E-shaped leaf springs 11, 11 are arranged parallel to each other on an axis of the supporting rod 6. Each E-shaped leaf spring 11 has side spring pieces 13, 13 having free ends, which are secured to the fixed frames 18, 18 by the bolts 15, 15. The E-shaped leaf spring 11 further has a central spring piece 14 having a free end to which the supporting rod 6 is secured. The fixed frames 18, 18 are supported respectively by the support pedestals 12, 12 shown in FIG. 1.

Figure 3:
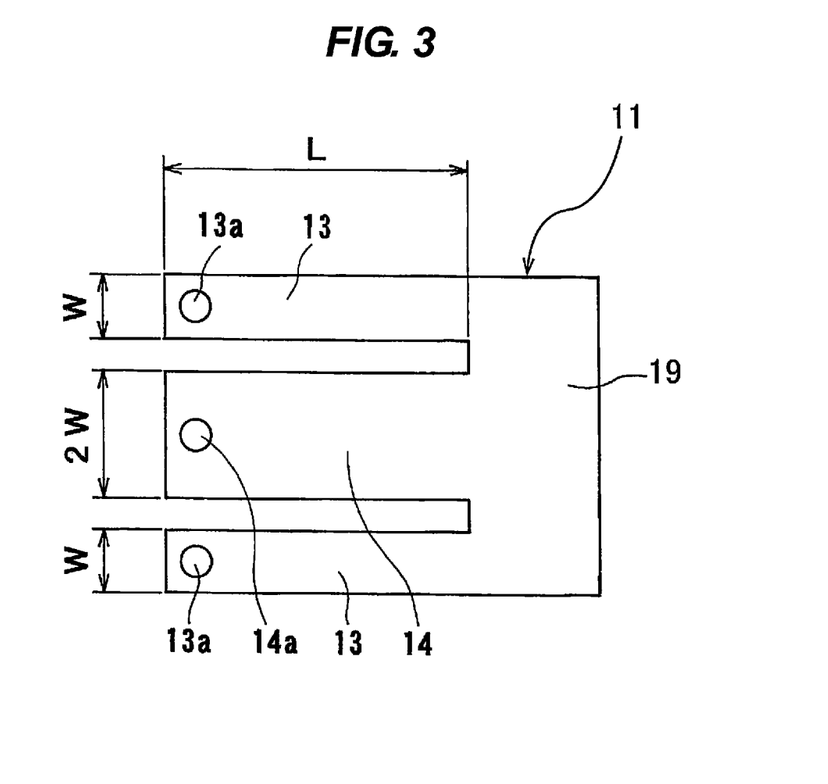
FIG. 3 is a plan view of an E-shaped leaf spring shown in FIG. 2.

FIG. 3 is a plan view of the E-shaped leaf spring shown in FIG. 2. As shown in FIG. 3, the E-shaped spring 11 includes a pair of rectangular side spring pieces 13, 13, the rectangular central spring piece 14 located between the side spring pieces 13, 13, and a connecting portion 19 that connects ends of the side spring pieces 13, 13 with an end of the central spring piece 14. The pair of side spring pieces 13, 13 have the same shape and the same dimensions. Each side spring piece 13 has a length L from the connecting portion 19, and has a width W. The central spring piece 14 has a length L from the connecting portion 19, and has a width 2W. The connecting portion 19, the side spring pieces 13, and the central spring piece 14 have the same thickness. Therefore, a combined spring constant of the pair of the side spring pieces 13, 13 is the same as a spring constant of the central spring piece 14.

The E-shaped springs 11, each having the structure shown in FIG. 3, are disposed at positions shown in FIG. 2. Specifically, the bolts 15, 15 are inserted into holes 13a, 13a, which are formed in the free ends of the pair of side spring pieces 13, 13, to secure the free ends of the pair of side spring pieces 13, 13 to the fixed frames 18, 18, respectively. The supporting rod 16 is inserted into a hole 14a formed in the free end of the central spring piece 14, and the supporting rod 6 is secured to the free end of the central spring piece 14. That is, the free ends of the side spring pieces 13, 13 are secured to the fixed frames 18, and the free end of the central spring piece 14 is secured to the supporting rod 6. With these configurations, the side spring pieces 13, 13 function as fixed-member spring pieces whose one ends are secured to fixed members, while the central spring piece 14 functions as a movable-member spring piece whose one end movably supports the supporting rod 6. Two or more E-shaped springs 11 are arranged parallel to each other on the axis of the supporting rod 6 (in the example shown in FIG. 2, two E-shaped springs 11 are arranged).

With the configurations shown in FIG. 2, when a load is applied to the supporting rod 6 in its axial direction, both the side spring pieces 13, 13 as the fixed-member spring pieces and the central spring piece 14 as the movable-member spring piece are deformed. When these deformations occur in the side spring pieces 13, 13 as the fixed-member spring pieces and the central spring piece 14 as the movable-member spring piece of the one pair of E-shaped springs 11 which are parallel to each other, their circular motions are cancelled mutually, so that the supporting rod 6 is allowed to move only linearly in its axial direction. As a result, the probe 4 remains oriented in the same direction at all times with respect to an object 1, and the probe 4 moves linearly in the vertical directions.

Figure 4:
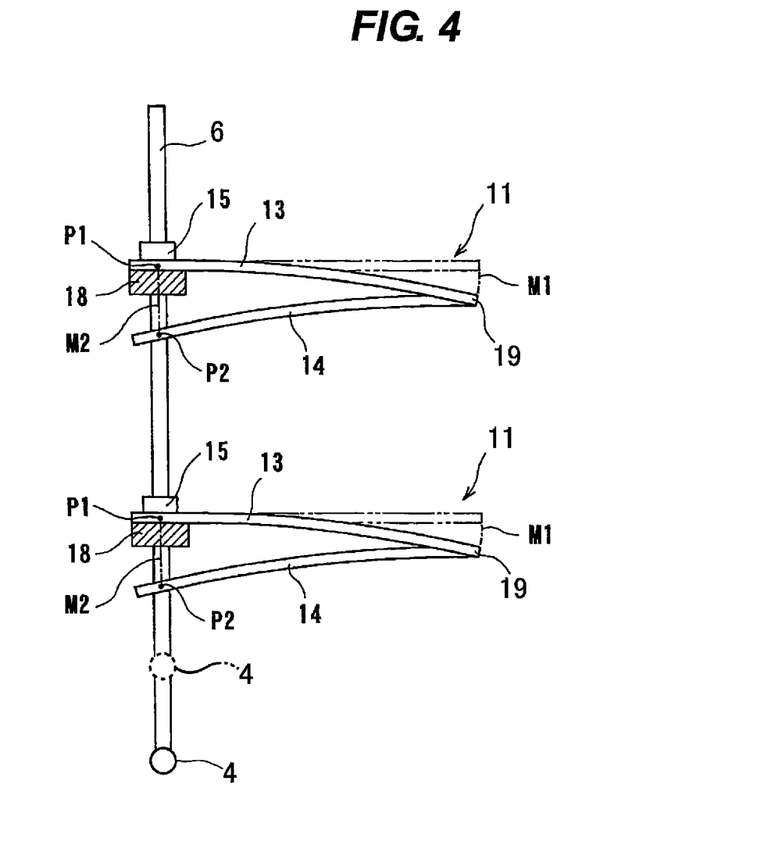
FIG. 4 is a schematic view showing a deformed state of E-shaped springs when a force is applied axially to a supporting rod.

FIG. 4 is a schematic view showing the deformed state of the E-shaped springs 11, 11 when a force is applied to the supporting rod 6 in its axial direction. As shown in FIG. 4, the side spring pieces 13 and the central spring piece 14 are deformed, while an edge of the connecting portion 19 makes a circular motion M1 around a fixed point P1 at which the side spring pieces 13 are secured to the fixed frames 18. A motion point P2, at which the supporting rod 6 is secured to the central spring piece 14, makes a circular motion M2 around the edge of the connecting portion 19. As a consequence, the point P2 is located below the point P1 in the vertical direction. Specifically, the circular motion of the side spring pieces 13, 13 as the fixed-member spring pieces and the circular motion of the central spring piece 14 as the movable-member spring piece are cancelled mutually, so that the supporting rod 6 and the probe 4 are allowed to move linearly only in the vertical directions.

As shown in FIG. 1, the electromagnetic-force generator 20 includes a coil 22 coupled to the supporting rod 6, and a magnetic-field generator 24 for generating a magnetic field. The coil 22 has a cylindrical shape, and a disk 23 is secured to a lower end of the coil 22. The disk 23 has a central portion fixed to the supporting rod 6, so that the coil 22, the supporting rod 6, and the probe 4 can move together linearly in the vertical directions. The magnetic-field generator 24 includes an annular permanent magnet 26, a cylindrical yoke 27 fixed to an inner circumferential surface of the permanent magnet 26, and a cylindrical yoke 28 fixed to an outer circumferential surface of the permanent magnet 26. The permanent magnet 26, the yoke 27, and the yoke 28 are concentric. The coil 22 is located between the yoke 27 and the yoke 28.

The magnetic field is formed between the yoke 27 and the yoke 28, and the coil 22 is placed in this magnetic field. When an electric current is passed to the coil 22, an electromagnetic force that moves the coil 22 in the vertical direction is generated. This electromagnetic force creates a load applied to the supporting rod 6 that is coupled to the coil 22. Therefore, the supporting rod 6 and the probe 4 are moved (or displaced) in the vertical direction when the supporting rod 6 and the probe 4 receive the load from the electromagnetic-force generator 20. This load can be controlled by the electric current to be passed to the coil 22.

The surface force measuring apparatus further includes a coarse adjustment stage (or an XYZ stage) 32 for moving the object 1 horizontally and vertically, and a fine adjustment stage 30 for performing accurate positioning of the object 1. The fine adjustment stage 30 is configured to move the object 1 only in the vertical directions. The fine adjustment stage 30 is mounted to the coarse adjustment stage 32, and the object 1 is placed on the fine adjustment stage 30. The fine adjustment stage 30 and the object 1 are moved horizontally and vertically together with each other by the coarse adjustment stage 32. The coarse adjustment stage 32 may be mounted to the fine adjustment stage 30, and the object 1 may be put on the coarse adjustment stage 32.

The coarse adjustment stage 32 may preferably comprise a ball screw mechanism as an actuator thereof, and the fine adjustment stage 30 may preferably comprise a piezoelectric device as an actuator thereof. The coarse adjustment stage 32 serves as a first positioning mechanism for performing rough positioning of the object 1, and the fine adjustment stage 30 serves as a second positioning mechanism for performing positioning of the object 1 more precisely than the coarse adjustment stage 32.

The probe 4, the supporting rod 6, the spring mechanism 8, the support pedestals 12, 12, the electromagnetic-force generator 20, the fine adjustment stage 30, and the coarse adjustment stage 32 are disposed in a vacuum chamber 40. The vacuum chamber 40 is coupled to a vacuum device which is not shown in the drawings. When the vacuum device is in motion, a vacuum is created in the vacuum chamber 40, so that the surface force can be measured under an environment with no influence of an ambient atmosphere. As a result, stable measurement is ensured. The vacuum chamber 40 is mounted to an anti-vibration table 42. This anti-vibration table 42 is configured to remove vibrations of the vacuum chamber 40.

A temperature regulator 46 having a circulation pipe 44 is disposed beneath the anti-vibration table 42. The circulation pipe 44 of the temperature regulator 46 is supplied with cooling water from a cooling-water supply source, which is not shown in the drawings. The cooling water is supplied into the circulation pipe 44, so that a space in the vacuum chamber 40 is kept at a predetermined temperature. The temperature regulator 46 serves to stabilize temperatures of devices (e.g., the probe 4, the supporting rod 6, the spring mechanism 8, the electromagnetic-force generator 20, etc.) located in the vacuum chamber 40, thus preventing them from being thermally expanded. The anti-vibration table 42 is disposed beneath the vacuum chamber 40 as illustrated in FIG. 1, while the anti-vibration table 42 may be disposed in the vacuum chamber 40, and the coarse adjustment stage 32 and the support pedestals 12, 12 may be disposed on the anti-vibration table 42.

As shown in FIG. 1, an operation controller 50 is disposed outside of the vacuum chamber 40. The operation controller 50 is a device for controlling operations of the electromagnetic-force generator 20, the fine adjustment stage 30, and the coarse adjustment stage 32.

A surface force acting between the object 1 and the probe 4 is determined by measuring a force required to separate the probe 4, which has been in contact with the object 1, away from the object 1. Specifically, the surface force is measured as follows. First, the object 1 is moved toward the probe 4 until the probe 4 is adsorbed to the object 1 by the surface force. Subsequently, with the probe 4 adsorbed to the object 1, the electric current is passed to the coil 22 while the electric current is gradually increased until the probe 4 is separated from the object 1. A value of the electric current that is passed to the coil 22 at a moment the probe 4 is separated from the object 1 is converted into the load (electromagnetic force) generated by the electromagnetic-force generator 20. This load is determined to be the surface force acting between the object 1 and the probe 4. The value of the electric current flowing through the coil 22 is converted into the load (electromagnetic force) generated by the electromagnetic-force generator 20 using a predetermined relational expression, which is stored in advance in the operation controller 50.

Figure 5:
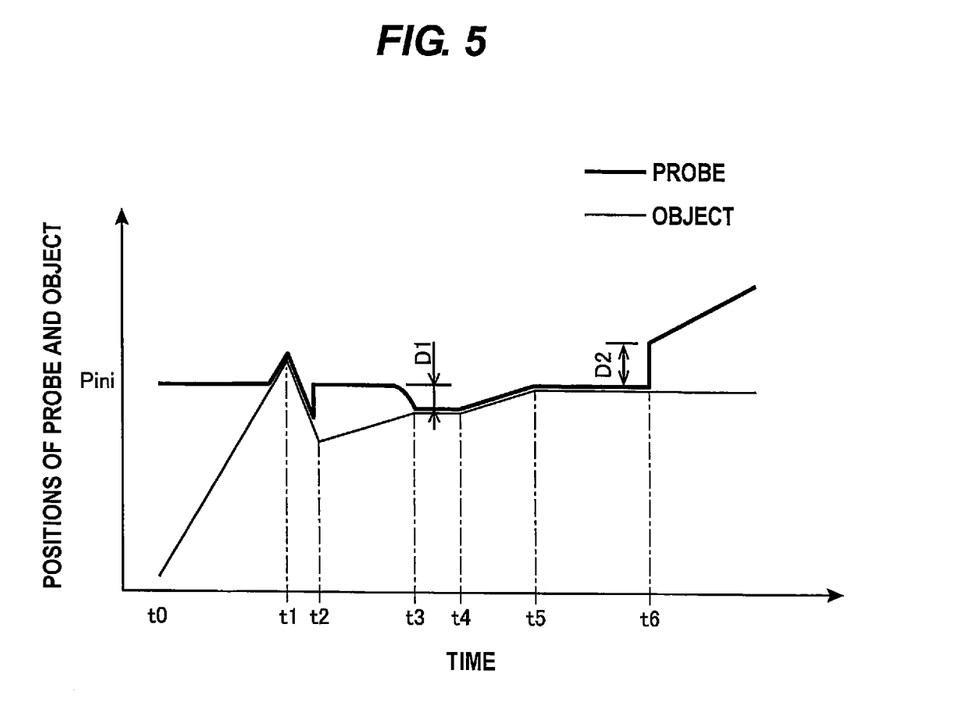
FIG. 5 is a graph showing displacement of a probe and an object along time axis.

FIG. 5 is a graph showing change in positions of the probe 4 and the object 1 when the surface force is measured. In FIG. 5, vertical axis represents vertical positions of the probe 4 and the object 1, and horizontal axis represents time. A thick line indicates a path of the probe 4 when it is moved, and a thin line indicates a path of the object 1 when it is moved. First, the coarse adjustment stage 32 is actuated to move the object 1 toward the probe 4 until the object 1 is brought into contact with the probe 4 (t0→t1). After the object 1 is brought into contact with the probe 4, the coarse adjustment stage 32 moves the object 1 in an opposite direction to separate the object 1 from the probe 4 (t1→t2). A point in time when the object 1 is brought into contact with the probe 4 and a point in time when the object 1 is separated from the probe 4 can be determined from the displacement of the probe 4 that is measured by the displacement measuring device 9.

Then, the fine adjustment stage 30 is actuated to move the object 1 gradually toward the probe 4 (t2→t3). As the object 1 approaches the probe 4, the surface force acts between the object 1 and the probe 4. The probe 4 is lowered against reaction forces of the E-shaped leaf springs 11, 11 until the probe 4 is finally brought into contact with the object 1 (t3). As a result, the probe 4 is displaced downwardly from its initial position Pini (a position at which the displacement of the probe 4 is zero). The force with which the object 1 attracts the probe 4 is referred to as "adsorption force". This adsorption force can be determined by multiplying the displacement (indicated by symbol D1 in FIG. 5) of the probe 4 from the initial position Pini by the spring constant of the E-shaped leaf springs 11, 11.

In this embodiment, the surface force is determined from the load (force) that is required for separating the probe 4 from the object 1. However, when the probe 4 is displaced downwardly from the initial position Pini, the reaction forces of the E-shaped springs 11, 11 act in a direction as to separate the probe 4 away from the object 1. Therefore, if the measurement of the surface force is started with the probe 4 displaced downwardly, an error may arise between a measured value of the surface force and the actual surface force. In order to minimize such an error, the probe 4 and the object 1 are elevated by the fine adjustment stage 30 until the probe 4 is returned to its initial position Pini with the probe 4 and the object 1 kept in contact with each other (t4→t5). When the probe 4 is at the initial position Pini, the flexure of the E-shaped springs 11, 11 is substantially zero, and therefore stresses in the E-shaped springs 11, 11 are also zero. In this state, the measurement of the surface force is started. Specifically, the supply of the electric current to the coil 22 is started.

The electric current passed to the coil 22 is gradually increased so as to increase an upward load applied to the supporting rod 6. This upward load acts on the probe 4 as a force that separates the probe 4 from the object 1. When the upward load becomes equal to the surface force, the probe 4 is separated from the object 1 (t6). The operation controller 50 obtains the value of the electric current flowing through the coil 22 at the moment the probe 4 is separated from the object 1, and determines a force that separates the probe 4 from the object 1 based on the value of the electric current obtained. The force that separates the probe 4 from the object 1 is referred to as "adhesion force". This adhesion force corresponds to the surface force.

Because the probe 4 is located right above the object 1, the surface force is generated in the vertical direction. The E-shaped leaf springs 11, 11 are configured to allow the supporting rod 6 to move only in the vertical direction. Therefore, the probe 4, which is secured to the supporting rod 6, moves in the vertical direction. In other words, the direction of the force that separates the probe 4 from the object 1 is aligned with the direction in which the surface force acts between the probe 4 and the object 1. Therefore, the surface force measuring apparatus can accurately measure the surface force acting between the object 1 and the probe 4.

The operation controller 50 can detect, from the displacement of the probe 4 measured by the displacement measuring device 9, the adsorption of the probe 4 to the object 1 and the separation of the probe 4 from the object 1. Specifically, the operation controller 50 determines a point in time when the probe 4 is adsorbed onto the object 1 based on a point in time when the downward displacement (indicated by symbol D1 in FIG. 5) of the probe 4 exceeds a predetermined first threshold value, and also determines a point in time when the probe 4 is separated from the object 1 based on a point in time when the upward displacement (indicated by symbol D2 in FIG. 5) of the probe 4 exceeds a predetermined second threshold value.

A process of converting a value of the electric current flowing through the coil 22 into a surface force will be described below by way of example. The operation controller 50 converts the electric current value into the surface force with use of the predetermined relational expression. This relational expression is obtained in advance as follows. A plurality of sample weights which have different weights are prepared, and one of the sample weights is attached to the supporting rod 6. Then, an electric current is passed to the coil 22, and is gradually increased until the sample weight is elevated by the electromagnetic-force generator 20. An electric current value at which the sample weight is elevated to the initial position, i.e., the height of the supporting rod 6 before the sample weight is attached thereto, is obtained. The electric current value obtained is associated with the weight of the sample weight. The same process is carried out on all the sample weights, so that a correlation between the electric current value and the weight is obtained. The weight of a sample weight corresponds to a surface force acting between the probe 4 and the object 1. Therefore, the correlation between the electric current value and the weight corresponds to the correlation between the electric current value and the surface force. The correlation between the electric current value and the surface force is expressed as a linear function. The linear function thus obtained is stored in advance in the operation controller 50. The operation controller 50 can determine the surface force by inputting an electric current value, obtained at the moment the probe 4 is separated from the object 1, into the linear function.

While the embodiment of the present invention has been described above, the present invention is not limited to the above embodiment, and various modification may be made within the range of the technical concept of the invention.

INDUSTRIAL APPLICABILITY

The present invention is applicable to a method and an apparatus for measuring a force acting between two material surfaces.

REFERENCE SIGNS LIST 1 object to be measured
4 probe
6 supporting rod
8 spring mechanism
9 displacement measuring device
10 measurement target
11 E-shaped leaf spring
12 support pedestal 13 side spring piece
14 central spring piece
15 bolt
18 fixed frame
19 connecting portion
20 electromagnetic-force generator
22 coil
23 disk
24 magnetic-field generator
26 permanent magnet
27, 28 yoke
30 fine adjustment stage
32 coarse adjustment stage
40 vacuum chamber
42 anti-vibration table
44 circulation pipe
46 temperature regulator
50 operation controller

The invention claimed is:

1. A surface force measuring method using an apparatus that includes a supporting member, a probe secured to the supporting member, a spring mechanism resiliently holding the supporting member and allowing the supporting member to move only linearly, and an electromagnetic-force generator configured to generate an electromagnetic force for applying a load to the supporting member, the surface force measuring method comprising:
   moving an object, to be measured, toward the probe until the probe is adsorbed to the object; then
   applying a load from the electromagnetic-force generator to the supporting member in a direction as to separate the probe from the object while gradually increasing an electric current supplied to the electromagnetic-force generator;
   obtaining a value of the electric current supplied to the electromagnetic-force generator when the probe is separated from the object; and
   converting the value of the electric current into a surface force acting between the probe and the object.

2. The surface force measuring method according to claim 1, further comprising:
   after the probe is adsorbed to the object, moving the probe and the object until the probe is returned to its initial position with the object kept in contact with the probe,
   wherein after the probe is returned to its initial position, the electromagnetic-force generator applies the load to the supporting member in the direction as to separate the probe from the object while the electric current supplied to the electromagnetic-force generator is gradually increased.

3. The surface force measuring method according to claim 1, further comprising:
   creating a vacuum in a space in which the object, the probe, the supporting member, the spring mechanism, and the electromagnetic-force generator are disposed.

4. The surface force measuring method according to claim 1, further comprising:
   regulating temperatures of the object, the probe, the supporting member, the spring mechanism, and the electromagnetic-force generator.

5. The surface force measuring method according to claim 1, wherein the value of the electric current is converted into the surface force using a predetermined relational expression which represents a correlation between the value of the electric current and the surface force.

6. A surface force measuring apparatus comprising:
   a supporting member;
   a probe secured to the supporting member;
   a spring mechanism resiliently holding the supporting member and allowing the supporting member to move only linearly;
   an electromagnetic-force generator configured to generate an electromagnetic force for applying a load to the supporting member;
   a displacement measuring device configured to measure a displacement of the probe;
   a first positioning mechanism configured to perform positioning of an object to be measured;
   a second positioning mechanism configured to perform positioning of the object more precisely than the first positioning mechanism; and
   an operation controller configured to control operations of the electromagnetic-force generator, the first positioning mechanism, and the second positioning mechanism,
   wherein the operation controller is configured to
      cause the second positioning mechanism to move the object toward the probe until the probe is adsorbed to the object, then
      cause the electromagnetic-force generator to apply a load to the supporting member in a direction as to separate the probe from the object while gradually increasing an electric current supplied to the electromagnetic-force generator,
      obtain a value of the electric current supplied to the electromagnetic-force generator when the probe is separated from the object, and
      convert the value of the electric current into a surface force acting between the probe and the object.

7. The surface force measuring apparatus according to claim 6, wherein the operation controller is configured to cause the second positioning mechanism to move the probe and the object, after the probe is adsorbed to the object, until the probe is returned to its initial position with the object kept in contact with the probe.

8. The surface force measuring apparatus according to claim 6, further comprising:
   a vacuum chamber in which the object, the probe, the supporting member, the spring mechanism, the electromagnetic-force generator, the displacement measuring device, the first positioning mechanism, and the second positioning mechanism are disposed.

9. The surface force measuring apparatus according to claim 6, further comprising:
   a temperature regulator configured to regulate temperatures of the object, the probe, the supporting member, the spring mechanism, the electromagnetic-force generator, the displacement measuring device, the first positioning mechanism, and the second positioning mechanism.

10. The surface force measuring apparatus according to claim 6, wherein the operation controller stores a predetermined relational expression which represents a correlation between the value of the electric current and the surface force, and is configured to convert the value of the electric current into the surface force using the predetermined relational expression.

* * * * *